(12) United States Patent
Zamora et al.

(10) Patent No.: US 6,575,888 B2
(45) Date of Patent: Jun. 10, 2003

(54) BIOABSORBABLE BRACHYTHERAPY DEVICE

(75) Inventors: Paul O. Zamora, Gaithersburg, MD (US); Robert A. Stern, Boxford, MA (US)

(73) Assignee: BioSurface Engineering Technologies, Inc., College Park, MD (US)

(*) Notice: Subject to any disclaimer, the term of this patent is extended or adjusted under 35 U.S.C. 154(b) by 0 days.

(21) Appl. No.: 09/769,194

(22) Filed: Jan. 24, 2001

(65) Prior Publication Data
US 2001/0044567 A1 Nov. 22, 2001

Related U.S. Application Data
(60) Provisional application No. 60/178,083, filed on Jan. 25, 2000.

(51) Int. Cl.⁷ .................................................. A61N 5/00
(52) U.S. Cl. ............................................................ 600/3
(58) Field of Search ..................... 600/8, 3; 424/1.11, 424/1.13, 422, 426; 514/411

(56) References Cited

U.S. PATENT DOCUMENTS

| | | | |
|---|---|---|---|
| 3,976,071 A | 8/1976 | Sadek | 128/260 |
| 4,697,575 A * | 10/1987 | Horowitz | 600/8 |
| 4,832,686 A | 5/1989 | Anderson | 604/49 |
| 4,883,666 A | 11/1989 | Sabel et al. | 424/422 |
| 4,897,268 A | 1/1990 | Tice et al. | 424/422 |
| 5,268,178 A * | 12/1993 | Calhoun et al. | 424/422 |
| 5,338,770 A | 8/1994 | Winters et al. | 523/112 |
| 5,391,547 A * | 2/1995 | Cole et al. | 424/1.13 |
| 5,463,010 A | 10/1995 | Hu et al. | 528/25 |
| 5,484,584 A | 1/1996 | Wallace et al. | 424/129 |
| 5,543,158 A | 8/1996 | Gref et al. | 424/501 |
| 5,626,862 A * | 5/1997 | Brem et al. | 424/1.11 |
| 5,656,297 A | 8/1997 | Bernstein et al. | 424/484 |
| 5,662,960 A | 9/1997 | Hostettler et al. | 427/2.3 |
| 5,736,152 A * | 4/1998 | Dunn | 424/426 |
| 5,789,018 A | 8/1998 | Engelson et al. | 427/2.3 |
| 5,811,447 A * | 9/1998 | Kunz et al. | 514/411 |
| 5,846,565 A | 12/1998 | Brem et al. | 424/486 |
| 5,876,452 A | 3/1999 | Athanasiou et al. | 623/16 |
| 5,993,374 A * | 11/1999 | Kick | 600/8 |
| 5,997,463 A | 12/1999 | Cutrer | 600/8 |
| 6,007,475 A | 12/1999 | Slater et al. | 600/8 |
| 6,080,099 A * | 6/2000 | Slater et al. | 600/8 |
| 6,099,458 A | 8/2000 | Robertson | 600/8 |
| 6,132,359 A | 10/2000 | Bolenbaugh | 600/8 |
| 6,159,143 A | 12/2000 | Lennox | 600/4 |
| 6,163,947 A | 12/2000 | Coniglione | 29/458 |
| 6,168,777 B1 | 1/2001 | Greff et al. | 424/1.25 |
| 6,174,330 B1 | 1/2001 | Stinson | 623/1.34 |
| 6,248,057 B1 * | 6/2001 | Mavity et al. | 600/3 |

* cited by examiner

Primary Examiner—Eric F. Winakur
Assistant Examiner—Nikita R Veniaminov
(74) Attorney, Agent, or Firm—Stephen A. Slusher; Peacock, Myers & Adams

(57) ABSTRACT

A bioabsorbable brachytherapy device includes a tubular housing with sealed ends and an enclosed radioactive material. The radioactive material includes a radioisotope, such as palladium-103 or iodine-125. The tubular housing is made from a biocompatible and bioabsorbable polymeric material, and is sealed by means such as heat welding or solvent fixing. The device may further include a radiopaque medium and one or more therapeutic drugs.

27 Claims, 5 Drawing Sheets

BIOABSORBABLE BRACHYTHERAPY DEVICE

CROSS-REFERENCE TO RELATED APPLICATIONS

This application claims the benefit of the filing of U.S. Provisional Patent Application Ser. No. 60/178,083, entitled Biodegradable Brachytherapy Source, to Paul O. Zamora and Robert A. Stern, filed on Jan. 25, 2000, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Grant No. R43 CA82030-01 awarded by the National Cancer Institute of the National Institutes of Health of the U.S. Department of Health and Human Services.

This application is related to U.S. patent application Ser. No. 09/361,553, entitled "Absorbable Brachytherapy and Chemotherapy Delivery Devices and Methods," to William G. Mavity, Robert A. Stern, Shigemasa Osaki and Paul O. Zamora, filed on Jul. 27, 1999, and the specification thereof is incorporated herein by reference.

BACKGROUND OF THE INVENTION

1. Field of the Invention (Technical Field)

This invention relates to methods, devices and systems for radiation delivery devices and combination radiation and drug delivery devices, and particularly methods, devices and systems for absorbable radiation delivery devices and combination radiation and drug delivery devices having elements that will be absorbed in tissue over time.

2. Background Art

Note that the following discussion refers to a number of publications by authors and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A number of techniques have been utilized or proposed to treat tumor growth, including radiation therapy, chemotherapy, and other treatment modalities. Brachytherapy, a form of radiation therapy, relies on implanting a radiation source in the body to provide localized treatment, as contrasted, for example, with treating a site from a distance by external beam radiation. In prostate brachytherapy, radiation is delivered by small "seeds" placed within the area being treated. Such placement minimizes the risk of affecting nearby tissue, while still delivering adequate radiation to destroy diseased cells.

In general, radioactive materials such as palladium-103 (Pd-103) and iodine-125 (I-125) are used, which have a relatively short half-life and emit low energy X-rays. A variety of different types of brachytherapy devices have been used to treat cancer and various types of tumors in human or animal bodies. Art conventional brachytherapy devices are contained in small metal capsules, generally made of titanium or stainless steel, and are welded or use adhesives to seal in the radioactive material.

The art conventional brachytherapy devices generally cannot be removed after placement. Thus they remain in the body even after the effective radiation dose has been delivered. The presence of these metallic brachytherapy devices can interfere with subsequent diagnostic X-rays or other imaging modalities, since they are radiopaque. In addition, these brachytherapy devices can interfere with other treatment modalities, such as thermal ablation or external beam radiation. Further, metallic brachytherapy devices are generally of a different density than that of the tissue in which they are placed, and can migrate after placement, both while still effectively emitting therapeutic radiation or after the radioactive source has decayed. Thus the devices may enter the lymphatic system or otherwise move to a position within the body that may cause medical complications, potential diagnostic confusion and the like.

One type of conventional brachytherapy device 1 is shown in FIG. 1, in which the device 1 contains a therapeutic amount of a radioisotope 2 disposed in a carrier 3. The radioisotope-containing carrier 3 is in a cavity 5 of a cylindrical casing 4. Casing 4, made of a metal such as stainless steel or titanium, is sealed at ends 6 and 7, typically by welding.

Another type of conventional brachytherapy device 10, disclosed in U.S. Pat. No. 4,891,165, is shown in FIG. 2 and employs two metal sleeves 12 and 14. Each of the sleeves has one closed end 16 and 18, with sleeve 14 having an outer diameter that is smaller than the inner diameter of the sleeve 12, permitting the sleeve 14 to slide inside sleeve 12. A radioactive source, such as pellets, can be placed inside the smaller sleeve 14, and then the larger external sleeve 12 slid over the smaller sleeve 14. The brachytherapy device 10 is permanently sealed, such as by welding.

Another conventional brachytherapy device 30, disclosed in U.S. Pat. No. 4,784,116, is shown in FIG. 3 and uses a single metal tube 32 which has metal end caps 34 and 36 inserted at the ends 38 and 40. The tube 30 contains the radioactive source. The ends 38 and 40 are welded, or adhesively secured, to the end caps 34 and 36 to seal the brachytherapy device 30.

Yet another conventional brachytherapy device 50, disclosed in U.S. Pat. No. 5,683,345, is shown in FIG. 4, has metal end plugs 52 and 54 that are slid into the open ends of a metal tube 56. The end plugs 52 and 54 are adhesively fixed and the metal of tube 56 then bent around the end plugs 52 and 54, or the end plugs 52 and 54 are welded to the tube 56.

Another conventional brachytherapy device 70 is shown in FIG. 5, which employs a metal tube 72 with ends 74 and 76. One end 74 of the tube 72 is welded, forming a metal weld bead 78 sealing the end 74. After placement of the radioactive material, the end 76 is welded forming metal bead 80 closing off end 76.

Yet another metal brachytherapy device 90, disclosed in U.S. Pat. No. 6,132,359, is shown in FIG. 6, which depicts metal case 94 with a center portion 96 and two end portions 98, and containing a radioactive source 92. Device 90 may be made by swaging one end portion 98 of casing 94, then welding swaged end portion 98 to provide a weld seal 100. After placement of the radioactive source 92 within the case 94, the second end portion 98 of casing 94 is then swaged and welded to provide a weld seal 102. While this configuration is purported to provide a more uniform radiation dose, it still utilizes a permanently-placed metal device.

Each of the foregoing devices is expensive and difficult to manufacture, involving a very precise welding step on a highly radioactive component, requiring shielding, robotics and other complex steps. In addition, quality control on such radioactive metal sources is difficult and time consuming.

The preparation of biodegradable radioactive materials is described in U.S. Pat. Nos. 5,256,765 and 5,194,581. In these materials, a radioisotope may be bound to a biodegradable polymeric matrix where the purpose is usually to provide for controlled release of the radioactive material over time. Such biodegradable radioactive materials are generally not useful for brachytherapy since they release the radioactive material rather than localize it at the desired treatment site.

In another approach, disclosed in co-pending and co-owned application Ser. No. 09/361,553, a radiation delivery component and a drug delivery component immobilized on a bioabsorbable structure is disclosed. The bioabsorbable structure has a predefined persistence period, such that it will remain sufficiently intact after implantation at a target site in patient tissue so that it can localize or sequester the radionuclide at the target site for a minimum threshold time, and further release or disperse the drug, which may be a chemotherapeutic agent, over a complimentary time. The minimum threshold time will usually depend at least in part on the half-life of the radionuclide. In particular, the predetermined persistence period of the bioabsorbable structure will usually be substantially longer than the half-life of the radionuclide, usually being at least two times longer, preferably being at least four times longer, and often being at least ten times longer. In this way, the radionuclide is not released from the bioabsorbable structure until after the persistence period has passed, so that the maximum effect of the radiation is limited to the target, and potential systemic or clearance organ dosage to the patient is below a known or predicted level of safety.

The use of biodegradable or bioerodible materials to provide sustained or controlled release of chemotherapeutic or other drugs, including bioactive drugs, has been known for a number of years. Biodegradable implants for the controlled release of hormones, such as contraceptive hormones, were developed over twenty years ago, and have been used as birth control devices. Biodegradable or bioerodible materials employed for controlled release of drugs include polyanhydrides, polyglycolic acid, polylactic/polyglycolic acid copolymers, polyhydroxybutyrate-valerate and other aliphatic polyesters, among a wide variety of polymeric substrates employed for this purpose. Biodegradable implantable materials, some of which have been used in drug delivery systems, are described in U.S. Pat. Nos. 5,656,297; 5,543,158; 5,484,584; 4,897,268; 4,883,666; 4,832,686; and 3,976,071. U.S. Pat. No. 5,876,452 describes biodegradable polymeric material, such as polyanhydries and aliphatic polyesters, providing substantially continuous release of bioactive drugs, including bi-phasic release of bioactive drugs.

The synergistic effect of combined radiation and chemotherapy has long been appreciated, and is a standard modality of cancer therapy. Prior art methods have frequently employed systemic chemotherapy, where chemotherapy drugs are administered intravenously, orally or by other systemic means, and external radiotherapy is employed, such as external beam radiation. In one instance, biodegradable polymer implants for the treatment of cancer, containing the cancer chemotherapeutic drug carmustine, have been used with concurrent external beam radiation, and found to increase survival in patients with metastatic brain tumors. (Ewend M G, Williams J A, Tabassi K, et al. Local delivery of chemotherapy and concurrent external beam radiotherapy prolongs survival in metastatic brain tumor models. *Cancer Res* 1996; 56(22):5217–5223) Conventional systemically administered chemotherapeutic agents have also been used in conjunction with implanted brachytherapy devices.

SUMMARY OF THE INVENTION (Disclosure of the Invention)

The present invention is directed to a brachytherapy device for use in radiation treatment of an affected tissue region. In one embodiment, the brachytherapy device includes a radioactive material including a radioisotope and a sealed bioabsorbable polymeric housing containing the radioactive material. Thus the bioabsorbable polymeric housing may be of any shape or configuration, and may be made by any means known in the art, so long as it contains the radioactive material. In one embodiment, the bioabsorbable polymeric housing for containing the radioactive material is formed by at least one tube having an axis and two ends, with the at least one tube being sealed at each end. Where the bioabsorbable polymeric housing is a tube or tube-like structure with at least one end, it may further include bioabsorbable polymeric material fixed in each end of the tube.

The device may further include a radiopaque medium, which may be disposed on at least a portion of the external surface of the bioabsorbable polymeric housing, such as a tube, may be disposed within at least a portion of the structure of the bioabsorbable polymeric housing, such as a tube, or may be disposed within the radioactive material.

The radioactive material of the device may include a chelate which is chelated to the radioisotope. The chelate, particularly for Pd-103, may be a porphine or a porphyrin. Applicable radioisotopes include Pd-103 and I-125. The radioactive material may further include a bioabsorbable substrate, which may be a a fatty acid such as palmitic acid, lauric acid or myristic acid. In one embodiment, the bioabsorbable substrate has a melting temperature above about 40° C. but below the melting temperature of the bioabsorbable polymeric housing.

The bioabsorbable polymeric housing may be made from a biocompatible polymeric material such as polycaprolactone, poly(D,L-lactide) poly(L-lactide), polyglycolide, poly(dioxanone), poly(glycolide-co-trimethylene carbonate), poly(L-lactide-co-glycolide), poly(D,L-lactide-co-glycolide), poly(L-lactide-co-D,L-lactide) or poly(glycolide-co-trimethylene carbonate-co-dioxanone). In one embodiment, the persistence of the bioabsorbable polymeric housing within a living organism is in excess of ten half-lives of the radioisotope.

The device may further include an effective amount of a therapeutic drug which may be disposed on at least a portion of the external surface of the bioabsorbable polymeric housing, such as a tube, or may be disposed within at least a portion of the structure of the bioabsorbable polymeric housing, such as a tube. The therapeutic drug may be one or more radiosensitizer drugs, chemotherapeutic drugs, anti-angiogenesis drugs, hormones, or apoptosis inducing drugs. The device may also include one or more coating constituents admixed with the therapeutic drug, which may assist in adhering the therapeutic drug to the device, control the rate of release of the therapeutic drug or provide similar functions.

The invention further provides a method for radiation treatment of an affected tissue region in a patient, which method includes the steps of obtaining a radioactive material comprising a radioisotope, fabricating a bioabsorbable polymeric housing to contain the radioactive material, the housing being formed by at least one tube having an axis and two ends, placing the radioactive material within the at least one tube comprising the polymeric housing, and placing the polymeric housing containing the radioactive material in the affected tissue region of the patient. In this method, any of the components of the device described herein may be employed.

The invention further provides a method of manufacturing a brachytherapy device for use in the radiation treatment of an affected tissue region, which method includes the steps of providing a radioactive material, fabricating a bioabsorbable polymeric housing to contain the radioactive material, the housing being formed by at least one tube having an axis and two ends, and placing the radioactive material within the at least one tube comprising the polymeric housing. Such method may further include the steps of sealing one end of the at least one tube prior to placing the radioactive material within the at least one tube and sealing the remaining end of the at least one tube subsequent to placing the radioactive material within the at least one tube. In this method, any of the components of the device described herein may be employed.

The invention thus provides methods and devices for the delivery of localized radioactivity, and preferably also concurrent delivery of localized chemotherapeutic, bioactive or other drugs to patients for therapeutic purposes. These improved delivery devices deliver local radiation, and optionally local chemotherapeutic or bioactive drugs, and are degradable after implantation so that the devices largely or completely disappear from the treatment region over time. The outer surface of such devices, however, have sufficient permanence or persistence so that the radioactive source material remains localized at the site of implantation at all times while the emitted radiation remains significant. Fabrication methods and techniques permit the construction of brachytherapy devices having a variety of forms, including devices sized the same as art conventional devices commonly used in brachytherapy.

The brachytherapy devices of this invention contain surfaces that can be easily coated with any of a variety of polymers, matrixes, coatings, eluting surfaces and the like. Because art conventional brachytherapy devices are metal, primarily stainless steel or titanium, the surface coatings which may be employed are limited by the metal substrate. There are a variety of coatings and the like known in the art which may be employed with polymeric materials. U.S. Pat. No. 5,338,770 describes methods and materials for coating biomedical devices and implants with poly(ethylene oxide) chains suitable for covalent attachment of bioactive molecules intended to counteract blood-material incompatibility. U.S. Pat. No. 5,463,010 describes membranes, including polymerized aliphatic hydrocyclosiloxane monomers, for use in coating biomedical devices and implants, and suitable for use as a substrate for covalent attachment of other molecules. U.S. patent application Ser. No. 09/098,072 describes methods useful in the present invention for coating polymeric and other materials. The full disclosures of each of these patents and pending application are incorporated herein by reference.

Accordingly, it is an object of this invention to provide a biocompatible and bioabsorbable brachytherapy source and device for use in treatment of disease, including radiation therapy of cancers.

It is a further object of this invention to provide a method for brachytherapy utilizing a source and device which approximates the size and shape of current art metal devices, and which may be similarly used and placed within a patient, but which are made of a bioabsorbable substance, and are absorbed into the body subsequent to substantial decay of the radiation.

It is further an object of this invention to provide a brachytherapy source and device in which the housing is not metallic, and minimally shields the effective dissemination of radiation, providing optimal radiation dosimetry to the tissues to be treated.

It is a further objection of this invention to provide a biocompatible and bioabsorbable brachytherapy source, including a sealed case and a radioactive component complex, wherein the radioactive component complex is biocompatible, and preferably bioabsorbable.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
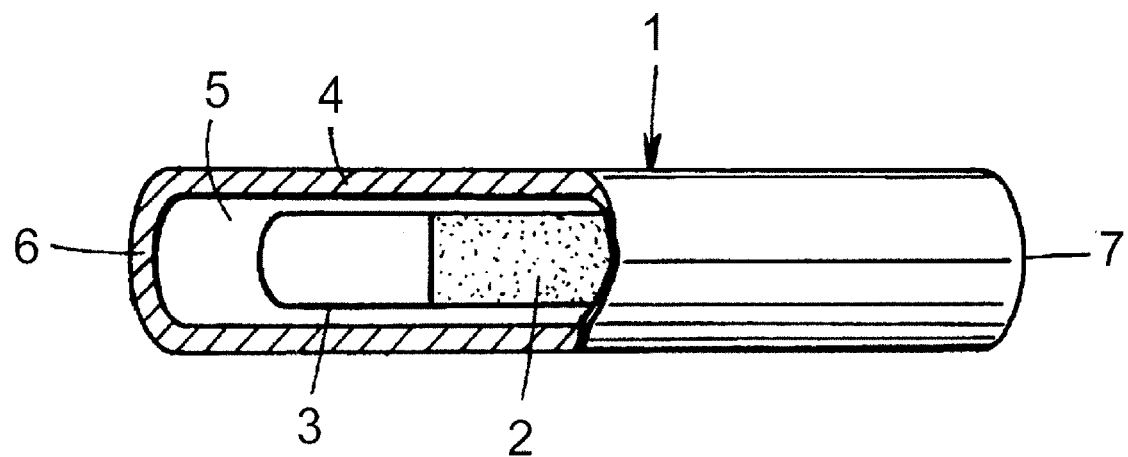
FIG. 1 is a drawing of an art conventional metal brachytherapy device.
Figure 2:
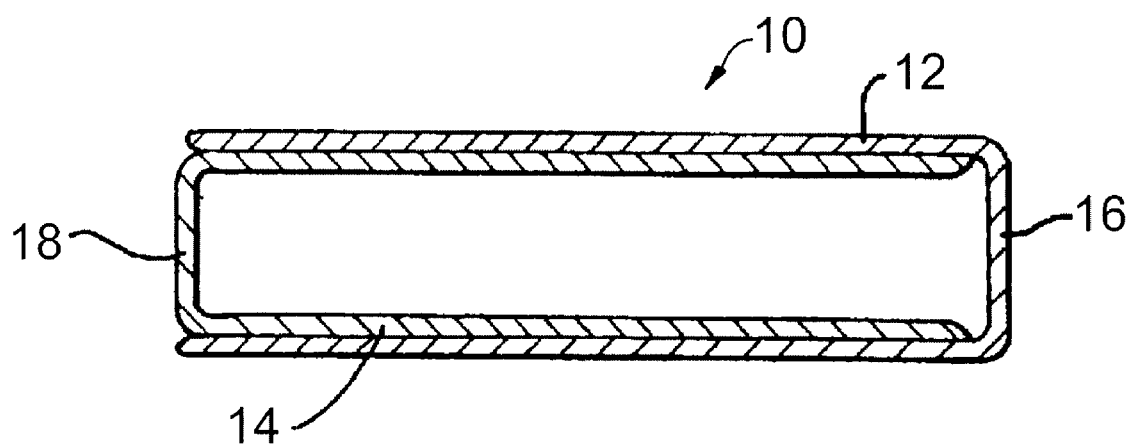
FIG. 2 is a drawing of an art conventional metal brachytherapy device.
Figure 3:
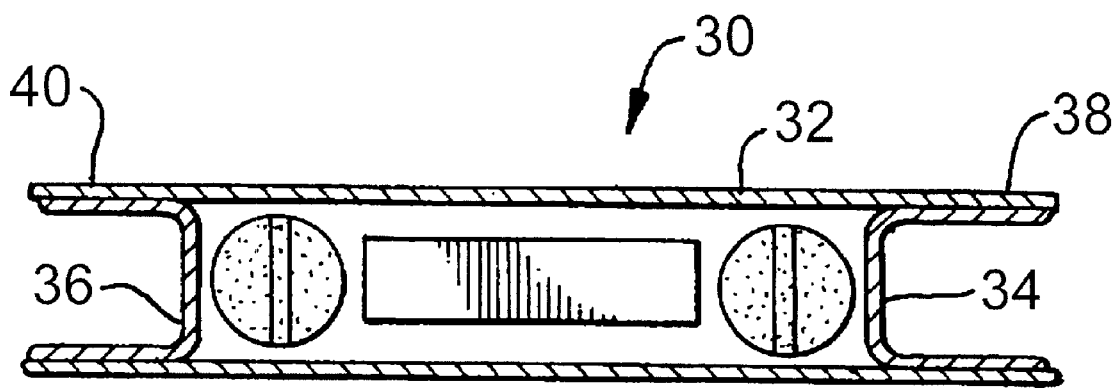
FIG. 3 is a drawing of an art conventional metal brachytherapy device.
Figure 4:
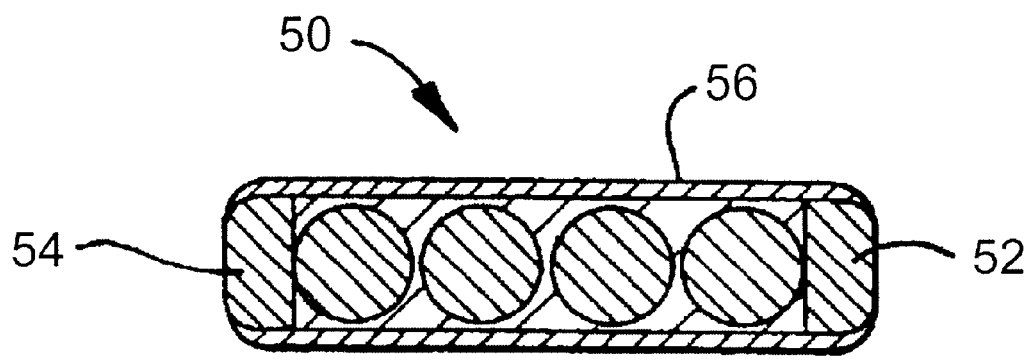
FIG. 4 is a drawing of an art conventional metal brachytherapy device.
Figure 5:
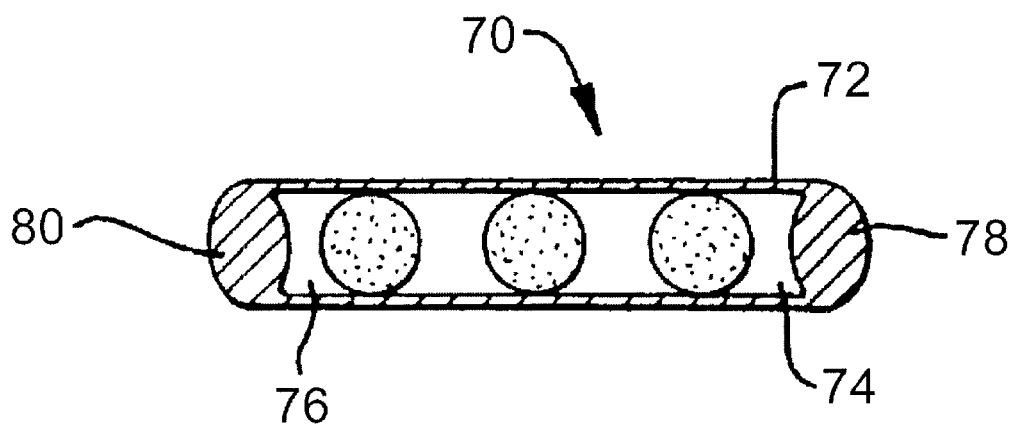
FIG. 5 is a drawing of an art conventional metal brachytherapy device.

DESCRIPTION OF THE PREFERRED EMBODIMENTS (Best Modes For Carrying Out the Invention)

For purposes of this patent, the following terms are defined:

The term "biocompatible polymer" refers to polymers which, in the amounts employed, are not toxic and are substantially non-immunogenic when placed internally in the patient.

The term "bioabsorbable polymer" refers to biocompatible polymers that are degradable, and preferably biodegradable, with a definable degradation rate. In general, a bioabsorbable polymer is capable of being broken down, in the body, into smaller constituents. Preferably the bioabsorbable polymer is, as it degrades into smaller constituents, metabolized or excreted through normal biological systems.

Hydrolysis is one mechanism by which some bioabsorbable materials are broken down following implantation within a living organism. Some bioabsorbable polymers may be composites, and may have a bioabsorption rate that varies over time. Examples of suitable bioabsorbable polymers may include poly-L-lactide, poly-D-lactide, polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly (alpha-hydroxy acid) and combinations thereof.

The term "radioisotope" refers to radioactive substances which may used for brachytherapy. In a preferred embodiment, palladium-103 (Pd-103) is used, but other radioisotopes may be employed, such as iodine-125 (I-125), cobalt-57, cobalt-60, cesium-137, iridium-192, yttrium-90 and the like. Pd-103 is a cyclotron-produced radioisotope with a 17-hour half-life. The average energy of Pd-103 is 21 keV and is close to that of I-125 (27 keV). The radioisotopes that may be employed are known to those skilled in the art of nuclear medicine, and are selected based upon considerations such as half-life, type of radiation, radiation dose and the like.

The term "radiopaque medium" refers to a biocompatible radiopaque material capable of being detected by X-rays and conventional radiographic methods, and optionally by magnetic resonance imaging and ultrasound imaging. Preferred radiopaque media include iodixanol, sold under the trade names Visipaque and Acupaque, and iohexol, sold under the trade names Omnipaque and Exypaque, which are Food and Drug Administration-approved iodine-containing radiopaque agents. Ethiodized oils, such as those sold under the trade names Lipiodol and Ethiodol, may also be employed. The foregoing are non-ionic, iodinated radiopaque agents. Other iodine-containing radiopaque agents include acetrizoate sodium, iobenzamic acid, iocarmic acid, iocetamic acid, iodamide, iodized oil, iodoalphionic acid, iodophthalein sodium, iodopyracet, ioglycamic acid, iomegiamic acid, iopamidol, iopanoic acid, iopentol, iophendylate, iophenoxic acid, iopromide, iopronic acid, iopydol, iopydone, iothalmic acid, iotrolan, ioversol, ioxaglic acid, ipodate, propyliodone and the like. Metal-containing contrast agents may also be employed, such as barium sulfate, which can be mixed with polymers such as polyurethane to increase radioopacity. Many of the iodine-containing radiopaque agents are water soluble, such as iodixanol and iohexol, while other iodine-containing radiopaque agents are largely or wholly insoluble in water, though they may be soluble in other solvents. Metallic elements with suitable biocompatibility and radiopacity include titanium, zirconium, tantalum, barium, bismuth and platinum. The preferred organic elements for biocompatibility and radiopacity are bromine, iodine, barium, and bismuth. Tantalum and platinum are used as stent components and barium sulfate and bismuth trioxide are used as radiopaque enhancements for polymer catheters.

Figure 7:
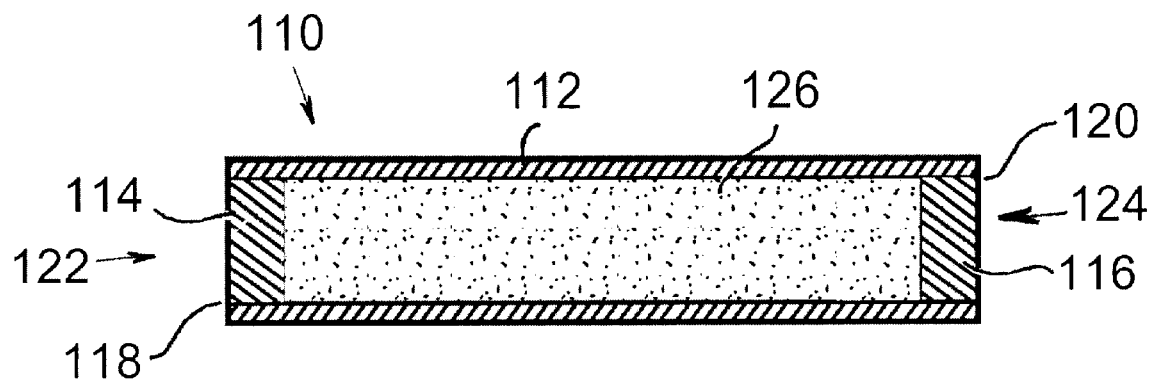
FIG. 7 is a drawing of a bioabsorbable polymer brachytherapy device of this invention.

Turning now to FIG. 7, a brachytherapy devise 110 in accordance with an embodiment of the present invention is shown. This device utilizes a tube 112 fabricated from a bioabsorbable polymer, and having ends 122 and 124, the tube 112 with ends 122 and 124 forming a housing. One end 122 is sealed with plug 114, which plug is sealed and affixed along seam 118 by means of heat welding, a biocompatible solvent, or other means known in the art. The tube 112 is then filled with a complex 126 that includes the radioisotope. The other end 124 is then closed using a plug 116, which is sealed and affixed along seam 120 by means of heat welding, a biocompatible solvent, or other means known in the art.

The housing comprising tube 112 and plugs 114 and 116 are made from a suitable bioabsorbable and biocompatible polymer, which may include polycaprolactone or another suitable polymeric material. Polycaprolactone can be melted to clear, viscous solution that can be extruded to tubes or punch pressed. Other suitable polymers include solvent-cast cellulose acetate butyrate and poly-lactide. The ring-opening polymerization of -caprolactone yields a semicrystalline polymer with a melting point of 59–64° C. and a glass-transition temperature of approximately 60° C. The polymer is tissue compatible and has been used as a biodegradable suture. Because the homopolymer has a degradation time on the order of 2 years, copolymers have been synthesized to accelerate the rate of bioabsorption. For example, copolymers of caprolactone with D,L-lactide yield materials with more rapid degradation rates. A block copolymer of caprolactone with glycolide, offering reduced stiffness compared with pure PGA, is sold as a monofilament suture by Ethicon, Inc. (Somerville, N.J.), under the trade name Monacryl.

The housing comprising tube 112 and the plugs 114 and 116 may be fabricated by any method known in the art, including extrusion, casting, punch pressing, injection molding, blow molding and milling. Alternative fabrication methods may also be employed. For example, tube 112 may be made from a sheet bioabsorbable polymer material, and rolled to form a tube, or may be made from a filament or thread-like bioabsorbable polymer material, and spun around a form to make a tube. Extrusion is a preferred technique, in which a viscous melt of the polymer is fed, under pressure, through a die in a continuous stream. Co-extrusion may be employed with copolymers.

Polylactide has degradation kinetics in the range of 12–16 months and polycaprolactone has a longer degradation profile, unless modified by use of copolymers. TABLE 1 sets forth certain of the properties of certain of the absorbable polymers that may be employed in the method of this invention, including polyglycolide (PGA), poly(L-lactide) (LPLA), -poly(D,L-lactide) (DLPLA), polycaprolactone (PCL), poly dioxanone (PDO), poly glycolide co-trimethylene carbonate (polyglyconate) (PGA-TMC), poly(lactide co-glycolide), for example composed of 85% polylactide and 15% polyglycolide (85/15 DLPLG), with 75/25 DLPLG, 65/35 DLPLG and 50/50 DLPLG referring to the relative percent composition of polylactide and polyglycolide. Polylactide exists in two stereo forms, signified by D or L for dexorotary or levorotary, or by D,L for the racemic mix.

TABLE 1

| Polymer | Melting Point (° C.) | Glass-Transition Temp (° C.) | Modulus (Gpa)[a] | Degradation Time (months)[b] |
| --- | --- | --- | --- | --- |
| PGA | 225–230 | 35–40 | 7.0 | 6 to 12 |
| LPLA | 173–178 | 60–65 | 2.7 | >24 |
| DLPLA | Amorphous | 55–60 | 1.9 | 12 to 16 |
| PCL | 58–63 | (−65)–(−60) | 0.4 | >24 |
| PDO | N/A | (−10)–0 | 1.5 | 6 to 12 |
| PGA-TMC | N/A | N/A | 2.4 | 6 to 12 |
| 85/15 DLPLG | Amorphous | 50–55 | 2.0 | 5 to 6 |
| 75/25 DLPLG | Amorphous | 50–55 | 2.0 | 4 to 5 |
| 65/35 DLPLG | Amorphous | 45–50 | 2.0 | 3 to 4 |
| 50/50 DLPLG | Amorphous | 45–50 | 2.0 | 1 to 2 |

[a]Tensile or flexural modulus.
[b]Time to complete mass loss. Rate also depends on part geometry.

The end plugs 114 and 116 are conveniently made of the same material as the tube 112, though other materials may be employed, so long as an appropriate seal may be made between the tube and plug, using a solvent, heat welding or other appropriate methods. The end plugs 114 and 116 are in the shape of a disk, with a diameter equal to or less than the interior diameter of the tube 112. The plugs 114 and 116 can be of any thickness, and are preferably of a thickness at least equal to the wall thickness of tube 112. The plugs 114 and 116 may be substantially thicker than the wall thickness of tube 112.

In one embodiment, the external diameter of tube 112 is 1.5 mm, and the length is 6 mm. The thickness of the wall of tube 112 is 0.5 mm, and the thickness of each of plugs 114 and 116 is 0.5 mm. Thus the interior volume is a cylinder with a diameter of 1 mm and a length of 5 mm, yielding a wet volume of a cylinder ($\pi R^2 L$) of 3.9 $\mu$l. The volume of a cylinder with an internal diameter of 0.7 mm and a length of 5 mm is 1.9 $\mu$l. This volume represents a "fill" volume of radioactive material into which complex 126, including the radioisotope, may be placed. In another embodiment, the external diameter of tube 112 is 1.1 mm, and the length is 5 mm. The thickness of the wall of tube 112 is 0.15 mm, so that the resulting internal diameter of tube 112 is 0.8 mm. The thickness of each of plugs 114 and 116 is approximately 0.25 mm, and the diameter of each of plugs 114 and 116 is approximately 0.7 mm.

In general, the exterior size of the device of FIG. 7 may be made any desired dimension, and may be made such that the exterior size is the same as any of the devices of FIG. 1 through FIG. 6, or any other known or subsequently developed brachytherapy device. For example, the device of FIG. 3 has external dimensions of approximately 0.8 mm×4.5 mm.

In one method of making the device of FIG. 7, the ends 122 and 124 may be heat welded by touching such end against a suitable heated surface, such as a heating iron. For use with polycaprolactone, a heating iron with a temperature of approximately 80° C. may be employed, which temperature is higher than the melting temperature of polycaprolactone. Alternatively, a suitable solvent may be employed. Plugs 114 and 116 may be made from a cylindrical rod of appropriate diameter, cut to suitable lengths.

In an alternative method of making the device of FIG. 7, each of plugs 114 and 116 may be made from melted bioabsorbable polymer, and may be fixed at ends 122 and 124 by means of injection or extrusion through a heated sleeve or other suitable means. In this method, no separate plug 114 or 116 is employed other than the melted material, and no additional or further welding or other sealing step is required.

Figure 6:
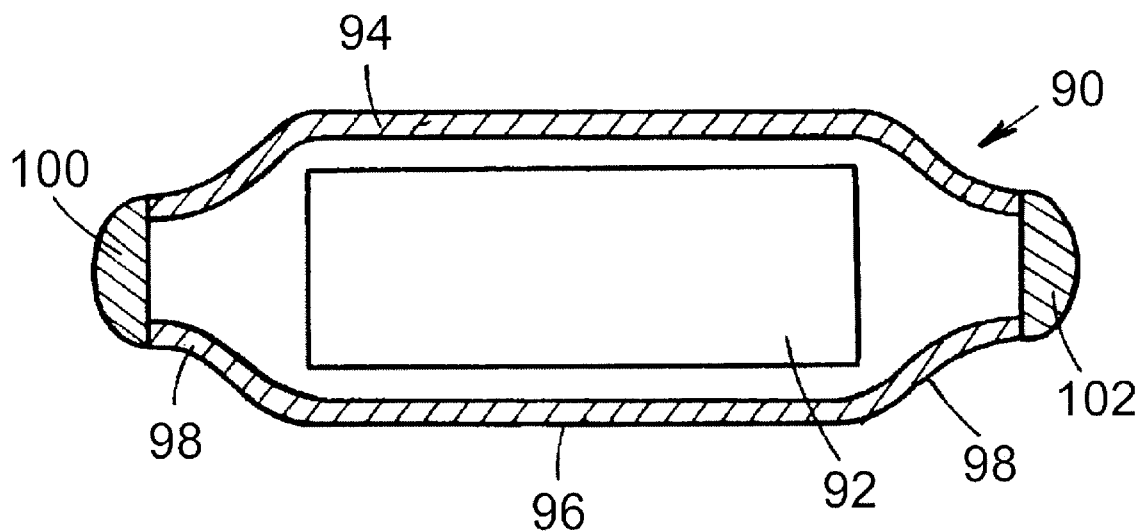
FIG. 6 is a drawing of an art conventional metal brachytherapy device.

In yet another alternative method of making a device of this invention, the ends 122 and 124 may be sealed by heating and compressing the ends, and optionally adding a quantity of molten bioresorbable polymer at each of ends 122 and 124, resulting in a device with an external configuration similar to that of the prior art device of FIG. 6. It should be noted that the device of FIG. 6 is made by swaging the cylinder 94, a metalworking technique requiring specialized equipment for devices the size of that depicted in FIG. 6. By contrast, the device of this invention may be similarly sized by using a heated die or other similar means, permitting substantially cheaper and simpler fabrication.

In one embodiment, the external diameter of tube 112 is 1.1 mm, and tube 112 is made from a tube of cast polycaprolactone with a wall thickness of approximately 0.15 mm, and an internal diameter of about 0.8 mm. A 5 mm length of polycaprolactone tube is cut. A plug 114 is made from a rod of cast polycaprolactone with a diameter of about 0.7 mm, and is inserted in end 122. The plug 114 is heat welded in place by touching against a heated electric plate, at a temperature of above about 80° C. A complex 126 is made by dissolving PdCl$_2$ into melted lauric acid at about 60° C., forming a complex of the lauric acid and Pd. The resulting melted and liquid complex 126 is injected into end 124, allowed to cool until the lauric acid has solidified, and a plug 116 is inserted into end 124 and heat welded in place by touching against a heated electric plate.

In one embodiment, the complex 126 is constituted such that (a) it does not contribution to dissolution of the bioabsorbable polymer of the tube 112 or plugs 114 or 116 of the device 110; (b) the radioisotope, or radioisotope chelate if provided, may be uniformly dispersed or suspended therein; (c) it is solid at room temperature and at body temperature; (d) it has a lower melting temperature than the bioabsorbable polymer; (e) it is non-toxic; and (f) it is itself bioabsorbable. The complex 126 thus preferably includes a bioabsorbable material. In one embodiment, the complex 126 includes a lipid or a fatty acid such as lauric acid, also know as dodecanoic acid. Lauric acid has a melting point of between about 40° C. and 44° C., substantially less than the melting point of polycaprolactone. Thus the complex 126 including the radioisotope and lauric acid may be melted at a suitable temperature, such as about 50° C. The liquid complex 126 may then be injected into a device 110 through end 124, it being understood that end 122 is sealed with plug 114. Following injection of the liquid complex 126, the complex is allowed to return to a temperature below the melting point of lauric acid, which may conveniently include use of refrigeration or a chilled gas, until complex 126 is solidified. End 124 may then be sealed by any of the means described herein or other means known to one of ordinary skill in the art.

Complex 126, in addition to fatty acids such as lauric acid, myristic acid or palmitic acid, may also include fill materials such as sorbitan alkanes, including sorbitan monopalitate, high molecular weight polyethylene glycol, and surfactants.

A preferred radioisotope for brachytherapy application is Pd-103. Pd-103 may be obtained from commercial sources as PdCl$_2$. The Pd-103 as PdCl$_2$ may be dissolved into an aqueous medium and complexed with a chelate. The resulting chelate-Pd-103 complex is then purified over a disposable hydrophobic-interaction column, such as a C18-SepPak column, and the solvent changed to an organic solvent. The organic solvent is removed by evaporation and the chelate-complex dissolved in a warmed solution of fatty acid or a similar material.

In another embodiment, the chelate may be dissolved in a small volume of ethanol, ethyl acetate, or other appropriate solvent and mixed with the fatty acid. In yet another embodiment, a solution containing the chelate-complex may be dispensed directly into biodegradable tubes and allowed to gel in situ.

In another embodiment, the Pd-103 is complexed to a chelate bound to a 3-D matrix by dipping or passing a solution of Pd-103 through the matrix. The matrix is optionally rinsed and then dried, and placed in the tube 112. In this embodiment, the complex 126 is based in the tube 112 as a solid, and not as a liquid or gel. Thus complex 126 may be any shape desired, so long as it fits within tube 112, including spherical shapes, as depicted generally in prior art devices of FIGS. 4 and 5. The complex 126 may also be a solid rod, which includes the radioisotope, and which is placed within tube 112.

In general, two different methods for introducing the radioisotope into complex 126 may be employed. One method utilizes chelating, while the second method utilizes adsorption.

For chelating, chelates may be attached to bead or core matrices forming a part of complex 126. Pd-103 in the form of $PdCl_2$ is obtained as a solution, in one commercially available form, the Pd-103 is in dilute ammonium hydroxide, with a specific activity of 60 Ci/g, activity of 50 mCi/ml, radiopurity of 99.95%. Thus 2 mCi, a suitable dose per device, is approximately 33 μg of material. The Pd-103 is attached to the chelate and the unbound radionuclide removed by solvent exchange or filtration.

Figure 8A:
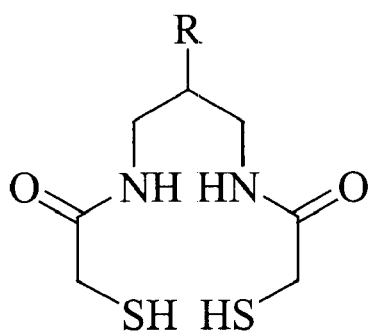
FIGS. 8a and b are chelates of this invention.
Figure 8:
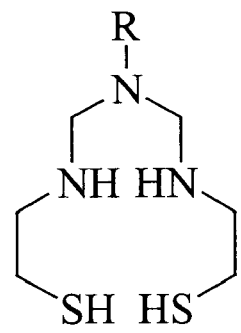

Palladium chelates are square planar and have chelation preferences for nitrogens and sulfur. As palladium is divalent it can also form ion pairs with carboxyl groups. Charge neutral complexes provide superior chelates, and two such complexes are shown in FIG. 8a and 8b. The chelate is covalently attached to the matrix and the matrix is then radiolabeled in situ. The matrix may be derived from a honeycomb polymer, such as that obtained from Osteobiologics, Inc. This polymer can be plasma coated and then subsequently conjugated to the chelates.

Any of a variety of chelates, known in the art, may be used to chelate palladium. In general, such chelates involve binding through sulfhydryl, amine, aldehyde or carboxyl groups. It is also possible and contemplated to employ chelates which are in turn attached to other molecules, such as monoclonal antibodies, peptides, enzymes, biotin and the like. These molecules may further contribute to preferred biodistribution, as for example excretion through the small intestine, once all or part of the external wall of device 110 has dissolved.

In an alternative method, the Pd-103 may be mixed with a hydrophobic Pd-chelating material and the Pd-chelate separated onto hydrophobic interaction chromatography bead matrices, such as a hydroxyalkoxypropyl dextran (sold under the trade name Sephadex). The Pd-chelate/bead matrix may then be mixed with a self-curing polymer and cast into rods or press-cast into rods.

Self-curing polymers may present potential problems as peroxides are most frequently used in these systems as accelerators, and the peroxides may be incompatible with Pd. Press casting may be of particular utility if a fatty acid or saturated triglyceride is used as a fill agent forming a part of complex 126. Palmitic acid may be utilized in this invention as it is both solid at body temperature and melts at about 45° C. This is above the melting temperature of polycaprolactone. The fatty acids lauric acid (C12:0) and myristic acid (C14:0) may also be utilized in this invention.

Figure 9:
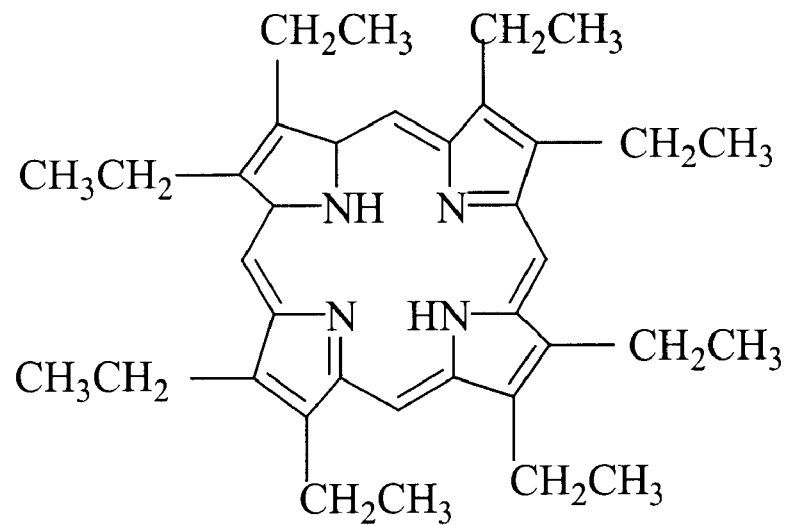
FIG. 9 is a chelate of this invention.

Pd-porphyrins are available from Porphyrin Products of Logan, Utah, including: Pd(II) Coproporphyrin I, Pd(II) Mesoporphyrin IX, Pd(II) meso-Tetra (N-methyl-4-Pyridyl) porphine, Pd(II) meso-Tetra (4-Pyridyl) porphine, Pd(II) meso-Tetra (4-Pyridyl) porphine. The non-metallated derivatives may be used with the metal binding performed under slightly basic conditions. In addition, 2, 3, 7, 8, 12, 13, 17, 18 octaethyl-21 H, 23-H porphine palladium may be used as a chelate. The unmetellated parent is shown in FIG. 9.

Efficient chelation is driven by molar excess of the chelate and thus a molar excess of at least 3:1 chelate to Pd may be employed to drive the reaction. If the chelate is attached to a structure prior to chelation to Pd, particles or honeycombed cylinders may be employed to increase the surface area so that a sufficient amount of chelate may be attached.

For other radioisotopes, such as I-125, a variety of chelates and chemical conjugates is well known in the art, and amply described in the literature. Any of a wide variety of conjugates to effect the desired biodistribution and routes of clearance of I-125, once all or part of the external wall of device 110 has dissolved, may be selected and used in the device and method of this invention.

Without intending to be bound by theory, it is believed that chelating the radioisotope by the means described herein will alter the biodistribution and route of clearance or excretion from the body, in the event of premature rupture or dissolving of the external wall of device 110, so that exposure to the kidneys and liver to radiation will be minimized, and the radioisotope will be excreted through the intestines. Chelating the radioisotope as described aids in efficient and rapid excretion of the metals, with minimal toxic side effects, once the external wall of device 110 has dissolved. Thus the chelates both provide a radiation safety factor and also provide for optimal excretion of the metals, once the radioactivity has substantially decayed.

In an alternative method, the Pd-103 can be adsorbed to biodegradable particles or other substrate material, and subsequently cast or otherwise formed as a rod or other structure in a biodegradable matrix.

Figure 10:
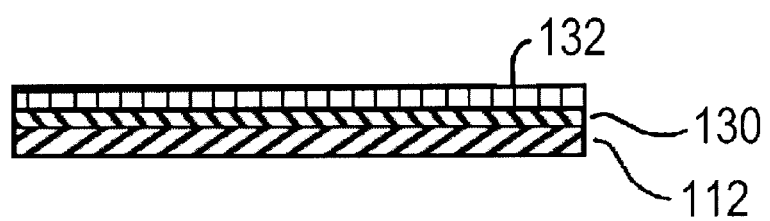
FIG. 10 is a drawing of a partial cross-section of a portion of a brachytherapy device of this invention.

It is frequently desirable to be able to verify the exact location of the devices of this invention within the tumor of the patient, such as by means of X-rays, including CT scanning, and alternatively by other means of detection, such as magnetic resonance imaging (MRI) and ultrasound imaging. The device of this invention, made of polymeric material, is relatively transparent to X-rays, and the quantity of metal employed as the radioisotope, such as palladium or iodine, is not sufficient to permit easy visualization. This may be overcome by the use of a radiopaque medium. Any of a variety of radiopaque agents, as described above, may be employed. In one embodiment, an iodine-based radiopaque agent is admixed with the other constituent elements forming complex 125. In another embodiment, a barium-based radiopaque agent is admixed with the other constituent elements forming complex 126. In yet another embodiment, the radiopaque agent forms a part of a coating over the device 110. FIG. 10 depicts a cross-section of a portion of the wall of device 110. In FIG. 10, a longitudinal cross-section of tube 112 is shown, with coatings 130 and 132 also depicted. Coating 130 includes a radiopaque medium, such as an iodine-containing or barium-containing radiopaque agent. For MRI or ultrasound detection, the radiopaque agent may include contrast agents specific for MRI or ultrasound detection, known to those of ordinary skill in the arts, such as gadolinium, various lipids and the like.

Coating 130 may include other constituent elements, including binders, adhesives, linkers, and the like, employed to attach the radiopaque agent to the surface of tube 112. Coating 132 is optionally provided, and may include a chemotherapeutic agent, including but not limited to bleomycin, busulfan, carboplatin, carmustine, cisplatin, cladribine, dactinomycin, daunorubicin, doxorubicin, estramustine, interferon, levamisole, methotrexate, mitomycin, paclitaxel, pentostatin, plicamycin, tamoxifen, vinblastine, vindesine and the like, a radiosensitizer drug such as 5-halo-uracil compounds, etanidazole, cisplatin and the like, an anti-angiogenesis compound such as thalidomide or tranilast, natural or synthetic peptide hormones including octreotide, and compounds that induce apoptosis including butyrate. Alternatively, coating 132 may include a plasma coating, such as with siloxane, which may prevent leaks from the device 110, and may further modulate or control the bioabsorption rate of the radiopaque medium of coating 130. The teachings and methods of U.S. Pat. Nos. 5,338,700 and 5,463,010, relating to siloxane and related plasma coatings, are incorporated by reference.

The drug delivery component of coating 132 preferably has a predefined release rate, which may be a continuous, bi-phasic or an otherwise modulated release rate. The drug is locally released at the site of the device, and is cleared from the patient by normal clearance and excretory functions. Depending on the disease, choice of radionuclide and choice of drug, the release rate of the drug may be predetermined so that the drug is released within the first two half-lives of the radionuclide, to provide an optimal high-level combination dose of radiation and drug to the site. Alternatively, the drug may be released over the period of predetermined persistence period of the bioabsorbable structure, such as by imbedding or combining the drug within the matrix of the bioabsorbable structure, to provide continued drug delivery to the site even after the radionuclide has substantially decayed.

Coatings 130 and 132 may conveniently be applied to the tube 112 prior to filing with complex 126 and sealing, or may be applied subsequent to filing and sealing. Particularly where siloxane or another coating to additionally seal the device 110 is employed, an ambient temperature radiofrequency plasma method, as described in the referenced patents, may be employed subsequent to filing and sealing.

The devices of this invention, including the device of FIG. 7, may be made such that the density of the device approximates that of normal and cancerous tissues. Typical metal brachytherapy devices, such as the devices of FIGS. 1 through 6, frequently have a greater density than that of the tissue within which they are placed. This difference in density contributes to movement of brachytherapy devices within the body, particularly in relatively soft tissues or organs. By approximating the density of the tissue in which the devices of this invention, including the device of FIG. 7, are placed, movement of the devices of this invention within the body is minimized. Further, the density of the devices of this invention may be altered, by appropriate selection of the component parts thereof, so that the density, as nearly as possible, approximates that of the tissue within which it is to be imbedded.

After preparing the devices of this invention, the amount of radioactivity is measured using a dose-calibrator, or similar measurement device, and wipe tests of the outside surface of the brachytherapy device tested to determine the amount of Pd-103 or other radionucleotide on the outside of the source. Only devices with an acceptably low amount of activity on the outside are used for the treatment of patients.

The brachytherapy devices are then implanted in a patient in a conventional manner, using methods substantially similar to those employed for treatment utilizing metal brachytherapy sources. Accordingly, the devices may be implanted singly, or may utilize suture strands, webs, meshes or other means to group the devices in a desired manner. If sutures, webs, meshes or similar means are employed, such means are biocompatible, and are preferably bioabsorbable. In one embodiment, each device of FIG. 7 contains between about 0.1 and 10 mCi of Pd-103, and preferably about 2 mCi of Pd-103. The number of devices used is determined by the radiation oncologist or other treating physician, based on the diagnosis, size of the tumor, location of the tumor, and other factors. Typically, between about 50 and 100 devices will be used per patient.

Pd-103 has a half-life of approximately 17 days, so that after ten half-lives, or about 170 days, less than 0.1% of the initial radioactivity remains. A device of this invention made of polycaprolactone would dissolve in vivo in about two years, with an anticipated half-life, to breaching of outer wall, of about 180 days. Thus the device of this invention, made of polycaprolactone, would retain integrity throughout the period of active emission of radiation.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A brachytherapy device for use in radiation treatment of an affected tissue region, the brachytherapy device comprising:
    a radioactive material comprising a radioisotope;
    a bioabsorbable polymeric housing containing the radioactive material, the housing being formed by at least one tube having an axis and two ends, the at least one tube being sealed at each end; and
    a radiopaque medium, wherein the radiopaque medium is disposed either on at least a portion of an external surface of the tube, within at least portion of a structure of the tube, or within the radioactive material;
    wherein there is no metal layer between the radioactive material and the bioabsorbable polymeric housing.

2. A brachytherapy device for use in radiation treatment of an affected tissue region, the brachytherapy device comprising:
    a radioactive material comprising a radioisotope and a chelate which is chelated to the radioisotope;
    a bioabsorbable polymeric housing containing the radioactive material, the housing being formed by at least one tube having an axis and two ends, the at least one tube being sealed at each end;
    wherein there is no metal layer between the radioactive material and the bioabsorbable polymeric housing.

3. The device of claim 2, wherein the chelate is selected from the group consisting of porphines and porphyrins.

4. A brachytherapy device for use in radiation treatment of an affected tissue region, the brachytherapy device comprising:
    a radioactive material comprising a radioisotope and a fatty acid bioabsorbable substrate;
    a bioabsorbable polymeric housing containing the radioactive material, the housing being formed by at least one tube having an axis and two ends, the at least one tube being sealed at each end;
    wherein there is no metal layer between the radioactive material and the bioabsorbable polymeric housing.

5. The device of claim 4, wherein the fatty acid is an acid selected from the group consisting of palmitic acid, lauric acid and myristic acid.

6. A brachytherapy device for use in radiation treatment of an affected tissue region, the brachytherapy device comprising:
    a radioactive material comprising a radioisotope and a bioabsorbable substrate, wherein the bioabsorbable substrate has a melting temperature above about 40° C. but below the melting temperature of the bioabsorbable polymeric housing, the bioabsorbable polymeric housing to be provided;
    a bioabsorbable polymeric housing containing the radioactive material, the housing being formed by at least one tube having an axis and two ends, the at least one tube being sealed at each end;
    wherein there is no metal layer between the radioactive material and the bioabsorbable polymeric housing.

7. The device of claims 1, 2, 4 or 6, wherein the bioabsorbable polymeric housing further comprises a plug of bioabsorbable polymeric material fixed in each end of the tube.

8. The device of claims 1, 2, 4, or 6, wherein the radioisotope is a member of the group selected from Pd-103 and I-125.

9. The device of claims 1, 2, 4, or 6, further comprising an effective amount of a therapeutic drug disposed on at least a portion of the external surface of the tube.

10. The device of claim 9, wherein the therapeutic drug is a drug selected from the group consisting of radiosensitizer drugs, chemotherapeutic drugs, anti-angiogenesis drugs, hormones, and apoptosis inducing drugs.

11. The device of claim 9, further comprising at least one coating constituent admixed with the effective amount of the therapeutic drug disposed on at least a portion of the external surface of the tube.

12. A method for radiation treatment of an effected tissue in a patient, the method comprising:
    obtaining a radioactive material comprising a radioisotope;
    providing a bioabsorbable polymeric housing to contain the radioactive material, the housing being formed by at least one tube having an axis and two ends;
    providing a radiopaque medium;
    incorporating the radiopaque medium within the bioabsorbable polymeric housing or within the radioactive material, or coating at least a portion of an external surface of the bioabsorbable polymeric housing with a composition comprising the radiopaque medium;
    placing the polymeric housing containing the radioactive material in the affected tissue region of the patient;
    wherein there is no metal layer between the radioactive material and the polymeric housing.

13. The method of claim 12, further comprising the step of coating at least a portion of the external surface of the bioabsorbable polymeric housing with a composition comprising a therapeutic drug.

14. The method of claim 13, wherein the therapeutic drug is a drug selected from the group consisting of radiosensitizer drugs, chemotherapeutic drugs, anti-angiogenesis drugs, hormones, and apoptosis inducing drugs.

15. A method of manufacturing a brachytherapy device for use in the radiation treatment of an affected tissue region, the method comprising:
    providing a radioactive material;
    fabricating a bioabsorbable polymeric housing to contain the radioactive material, the housing being formed by at least one tube having an axis and two ends;
    providing a radiopaque medium;
    either incorporating the radiopaque medium within the bioabsorbable polymeric housing, coating at least a portion of an external surface of the bioabsorbable polymeric housing with a composition comprising the radiopaque medium, or incorporating the radiopaque medium within the radioactive material; and
    placing the radioactive material within the at least one tube comprising the polymeric housing.

16. The method of claim 15, further comprising the step of coating at least a portion of the external surface of the bioabsorbable polymeric housing with a composition comprising a therapeutic drug.

17. The method of claim 16, wherein the therapeutic drug is a drug selected from the group consisting of radiosensitizer drugs, chemotherapeutic drugs, anti-angiogenesis drugs, hormones, and apoptosis inducing drugs.

18. A brachytherapy device for use in radiation treatment of an affected tissue region, the brachytherapy device comprising:
    a radioactive material comprising a radioisotope;
    a radiopaque medium, wherein the radiopaque medium is disposed either on at least a portion of an external surface of the housing, within at least a portion of a bioabsorbable polymeric housing, or within the radioactive material; and,
    a sealed bioabsorbable polymeric housing containing the radioactive material;
    wherein there is no metal layer between the radioactive material and the polymeric housing.

19. A brachytherapy device for use in radiation treatment of an affected tissue region, the brachytherapy device comprising:
    a radioactive material comprising a radioisotope and a chelate which is chelated to the radioisotope;
    a sealed bioabsorbable polymeric housing containing the radioactive material;
    wherein there is no metal layer between the radioactive material and the polymeric housing.

20. The device of claim 19, wherein the chelate is selected from the group consisting of porphines and porphyrins.

21. A brachytherapy device for use in radiation treatment of an affected tissue region, the brachytherapy device comprising:
    a radioactive material comprising a radioisotope and a fatty acid bioabsorbable substrate;
    a sealed bioabsorbable polymeric housing containing the radioactive material;
    wherein there is no metal layer between the radioactive material and the polymeric housing.

22. The device of claim 21, wherein the fatty acid is an acid selected from the group consisting of palmitic acid, lauric acid and myristic acid.

23. A brachytherapy device for use in radiation treatment of an affected tissue region, the brachytherapy device comprising:
    a radioactive material comprising a radioisotope and a bioabsorbable substrate, wherein the bioabsorbable substrate has a melting temperature above about 40° C. but below the melting temperature of the bioabsorbable polymeric housing, the bioabsorbable polymeric housing to be provided;
    a sealed bioabsorbable polymeric housing containing the radioactive material;
    wherein there is no metal layer between the radioactive material and the polymeric housing.

24. The device of claims 18, 19, 21 or 23, wherein the radioisotope is a member of the group selected from Pd-103 and I-125.

25. The device of claims 18, 19, 21 or 23, further comprising an effective amount of a therapeutic drug disposed on at least a portion of the bioabsorbable polymeric housing.

26. The device of claim 25, wherein the therapeutic drug is a drug selected from the group consisting of radiosensitizer drugs, chemotherapeutic drugs, anti-angiogenesis drugs, hormones, and apoptosis inducing drugs.

27. The device of claim 25, further comprising at least one coating constituent admixed with the therapeutic drug.

* * * * *